(12) United States Patent
Lekweuwa

(10) Patent No.: US 8,357,132 B1
(45) Date of Patent: Jan. 22, 2013

(54) URINE CAPTURING ASSEMBLY

(76) Inventor: Agatha N. Lekweuwa, Bronx, NY (US)

( * ) Notice: Subject to any disclaimer, the term of this patent is extended or adjusted under 35 U.S.C. 154(b) by 533 days.

(21) Appl. No.: 12/603,373

(22) Filed: Oct. 21, 2009

(51) Int. Cl.
*A61F 5/44* (2006.01)

(52) U.S. Cl. ............. 604/349; 604/67; 604/68; 604/69; 604/70; 604/71; 604/72; 604/358; 604/367; 604/386; 604/387; 604/365; 604/374; 604/375; 604/381; 604/384

(58) Field of Classification Search .................. 604/349, 604/358, 361, 367
See application file for complete search history.

(56) References Cited

U.S. PATENT DOCUMENTS

| | | | |
|---|---|---|---|
| 4,824,105 A | 4/1989 | Goldenberg | |
| 4,994,051 A * | 2/1991 | Walsh | 604/349 |
| 5,195,938 A | 3/1993 | Robertson | |
| 5,669,862 A | 9/1997 | Sayman | |
| 6,061,840 A * | 5/2000 | Alligator | 2/403 |
| D506,514 S | 6/2005 | Bernstein | |
| D516,638 S | 3/2006 | Felberg et al. | |
| 7,101,328 B2 | 9/2006 | Chiu | |
| 7,137,934 B2 | 11/2006 | Paramater | |
| 7,176,213 B2 | 2/2007 | Aranyi et al. | |
| 2008/0146419 A1 | 6/2008 | Chu | |

* cited by examiner

*Primary Examiner* — Tatyana Zalukaeva
*Assistant Examiner* — Ilya Treyger

(57) ABSTRACT

A urine capturing assembly includes a sleeve that has an upper edge, a lower edge and a perimeter wall extending between the upper and lower edges. The upper and lower edges define openings in the sleeve. A penis is positionable in the sleeve to direct urine from the penis toward the lower edge. A pouch has an open top end. The pouch is integrally coupled to the perimeter wall and the top end is positioned adjacent to the upper edge of the sleeve. A scrotum is positionable in pouch through the top end. A conduit is fluidly coupled to and extends between the sleeve and the pouch to direct urine held in the pouch into the sleeve. A collection bag is fluidly couplable to the lower edge of the sleeve to collect and retain urine.

6 Claims, 5 Drawing Sheets

URINE CAPTURING ASSEMBLY

BACKGROUND OF THE DISCLOSURE

Field of the Disclosure

The disclosure relates to urine leakage prevention devices and more particularly pertains to a new urine leakage prevention device for preventing the leakage of urine onto a person's body and for retaining the urine for disposal or testing.

SUMMARY OF THE DISCLOSURE

An embodiment of the disclosure meets the needs presented above by generally comprising a sleeve that has an upper edge, a lower edge and a perimeter wall extending between the upper and lower edges. The upper and lower edges define openings in the sleeve. A penis is positionable in the sleeve to direct urine from the penis toward the lower edge. A pouch has an open top end. The pouch is integrally coupled to the perimeter wall and the top end is positioned adjacent to the upper edge of the sleeve. A scrotum is positionable in pouch through the top end. A conduit is fluidly coupled to and extends between the sleeve and the pouch to direct urine held in the pouch into the sleeve. A collection bag is fluidly couplable to the lower edge of the sleeve to collect and retain urine.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
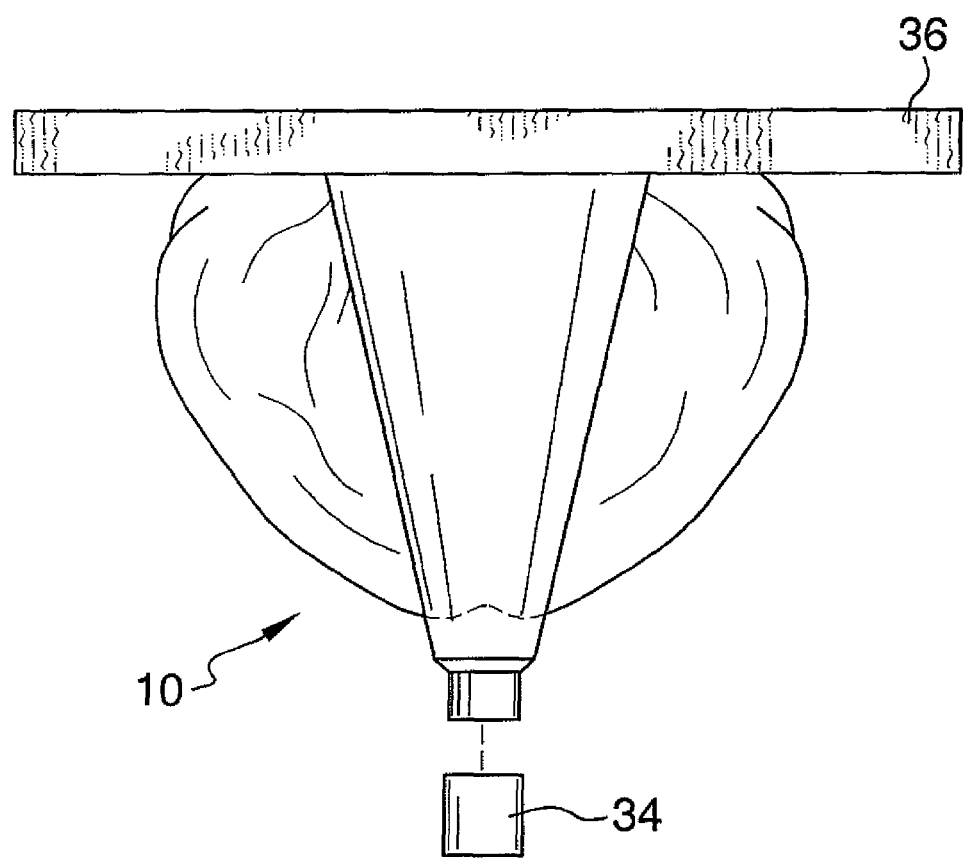
FIG. 1 is a front view of a urine capturing assembly according to an embodiment of the disclosure.
Figure 2:
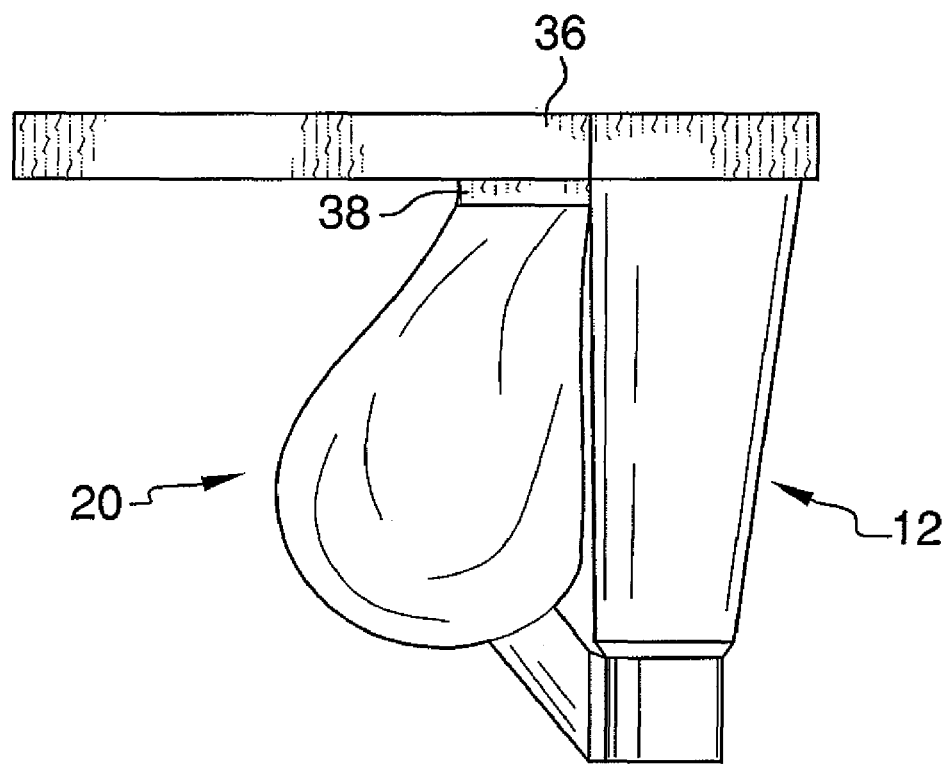
FIG. 2 is a side view of an embodiment of the disclosure.

With reference now to the drawings, and in particular to FIGS. 1 through 5 thereof, a new urine leakage prevention device embodying the principles and concepts of an embodiment of the disclosure and generally designated by the reference numeral 10 will be described.

Figure 5:
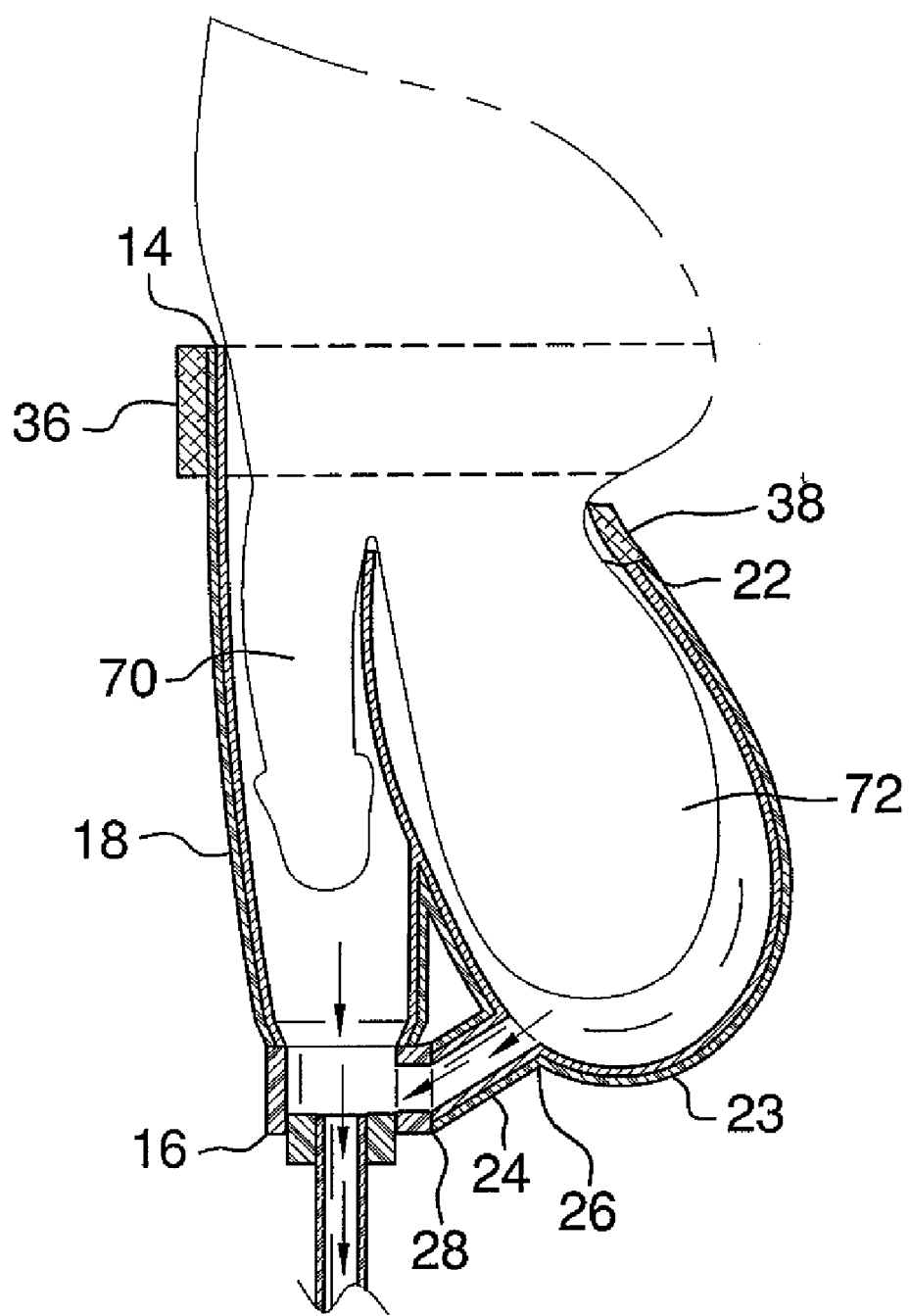
FIG. 5 is a cross-sectional view taken along line 5-5 of FIG. 4 of an embodiment of the disclosure.

As best illustrated in FIGS. 1 through 5, the urine capturing assembly 10 generally comprises a sleeve 12 that has an upper edge 14, a lower edge 16 and a perimeter wall 18 extending between the upper 14 and lower 16 edges. The upper 14 and lower 16 edges define openings in the sleeve 12. A penis 70 is positionable in the sleeve 12 to direct urine from the penis 70 toward the lower edge 16. A pouch 20 has an open top end 22. The pouch 20 is integrally coupled to the perimeter wall 18 so that the top end 22 is positioned adjacent to the upper edge 14 of the sleeve 12. A scrotum 72 is positionable in pouch 20 through the top end 22. The pouch 20 has a bottom wall 23. The pouch 20 and sleeve 12 each comprise a fluid impermeable material and may include multiple layers. As shown in FIG. 5, the perimeter wall 18 may be partially shared with the pouch 20.

Figure 3:
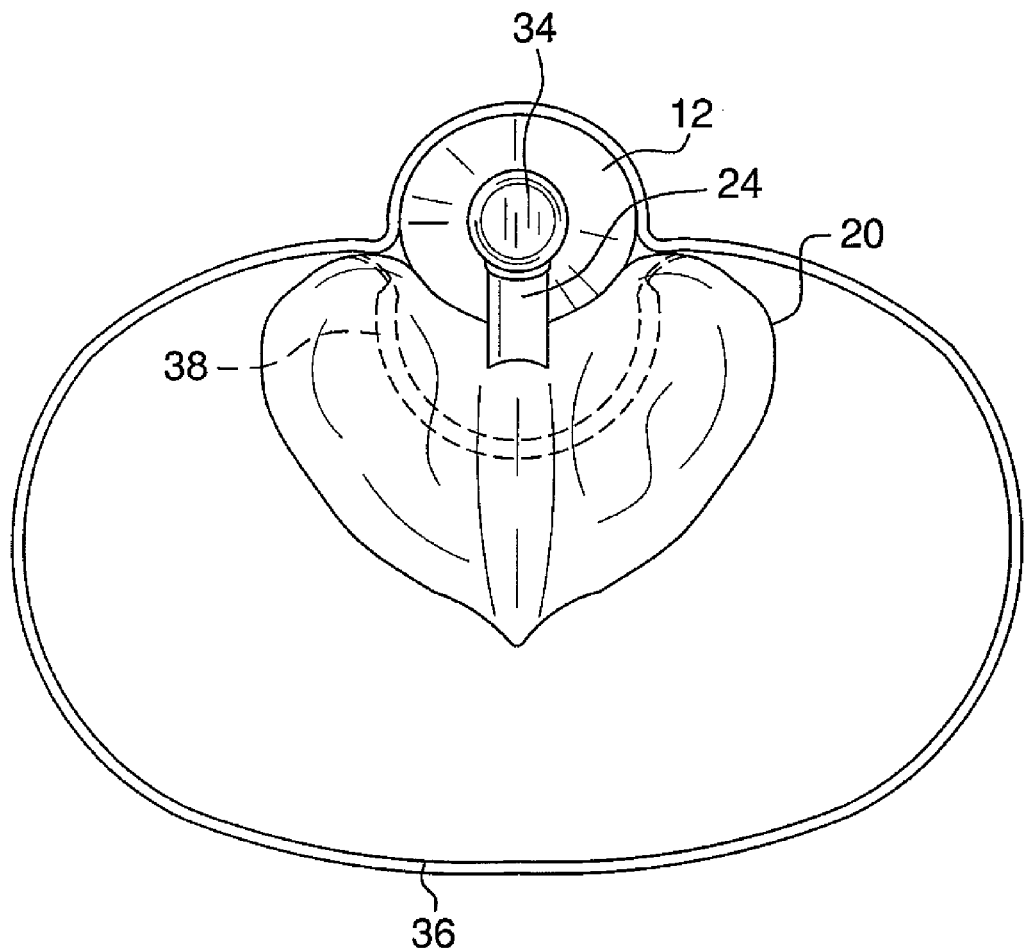
FIG. 3 is a bottom view of an embodiment of the disclosure.
Figure 4:
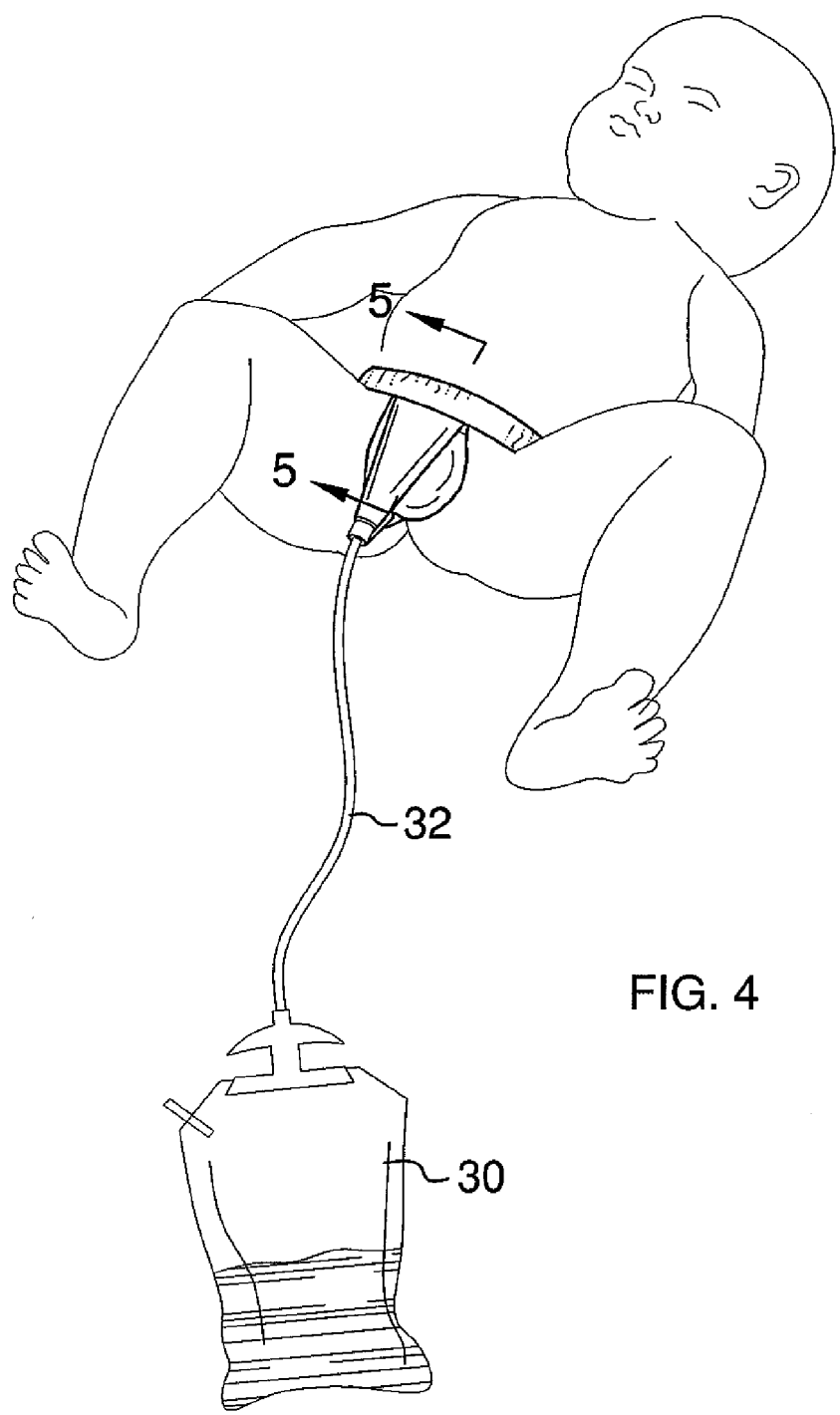
FIG. 4 is a perspective in-use view of an embodiment of the disclosure.

A conduit 24 is fluidly coupled to and extends between the sleeve 12 and the pouch 20 to direct urine held in the pouch 20 into the sleeve 12. The conduit 24 has a first end 26 attached to the pouch 22 adjacent to the bottom wall 23. The conduit 24 has a second end 28 attached to the sleeve 12 adjacent to the lower edge 16. The conduit 24 is angled downwardly from the pouch 20 to the sleeve 12 to direct fluid outwardly of the pouch 20. The pouch 20, as shown in FIG. 3, may be tapered toward the sleeve 12 to again encourage fluid flow toward the sleeve 12.

A collection bag 30 is fluidly coupled to the lower edge 16 of the sleeve 12 to collect and retain urine. The collection bag 30 may be fluidly coupled to the sleeve with a tube 32. A cap 34 may be provided for extending over the lower edge 16 when the collection bag 30 is not being used.

A strap 36 is attached to the sleeve 12 adjacent to the upper edge 14. The strap 36 is extendable around the penis 70 and scrotum 72 to retain the sleeve 12 in place and to prevent leakage outwardly of the sleeve 12. The strap 36 may be retained around the scrotum 72 by friction if the strap 36 is comprised of a resiliently stretchable material. Alternatively, the strap 36 may include two sections which are securable together to form a loop around the genitalia. A resiliently stretchable band 38 is attached to and extends along the top end 22 of the pouch 20. The band 38 retains the pouch 38 on the scrotum 72 and prevents urine from flowing outwardly of the pouch 20.

In use, the sleeve 12 and pouch 20 are positioned on the penis 70 and the scrotum 72 as stated above. The assembly will prevent the leakage of urine around the scrotum 72 when the penis 70 is retracted due to illness or obesity. Any urine flowing around the scrotum 72 will be directed into the sleeve to be carried to the collection bag 30.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A urine capturing assembly comprising:
   a sleeve having an upper edge, a lower edge and a perimeter wall extending between said upper and lower edges, said upper and lower edges defining openings in said sleeve, wherein a penis is positionable in said sleeve to direct urine from the penis toward said lower edge;

a pouch having an open top end, said pouch being integrally coupled to said perimeter wall, said top end being positioned adjacent to said upper edge of said sleeve, wherein a scrotum is positionable in pouch through said top end;

a conduit comprising a tube being fluidly coupled to and extending between said sleeve and said pouch to direct urine held in said pouch into said sleeve; and wherein a collection bag is fluidly couplable to said lower edge of said sleeve to collect and retain urine.

2. The assembly according to claim 1, wherein said conduit has a first end attached to said pouch adjacent to a bottom wall of said pouch, said conduit having a second end attached to said sleeve adjacent to said lower edge, said conduit being angled downwardly from said pouch to said sleeve.

3. The assembly according to claim 1, further including a strap being attached to said sleeve adjacent to said upper edge, said strap being extendable around the penis and scrotum to retain said sleeve in place.

4. The assembly according to claim 3, further including a resiliently stretchable band being attached to and extending along said top end of said pouch.

5. The assembly according to claim 1, further including a resiliently stretchable band being attached to and extending along said top end of said pouch.

6. A urine capturing assembly comprising:

a sleeve having an upper edge, a lower edge and a perimeter wall extending between said upper and lower edges, said upper and lower edges defining openings in said sleeve, wherein a penis is positionable in said sleeve to direct urine from the penis toward said lower edge;

a pouch having an open top end, said pouch being integrally coupled to said perimeter wall, said top end being positioned adjacent to said upper edge of said sleeve, wherein a scrotum is positionable in pouch through said top end, said pouch having a bottom wall;

a conduit comprising a tube being fluidly coupled to and extending between said sleeve and said pouch to direct urine held in said pouch into said sleeve, said conduit having a first end attached to said pouch adjacent to said bottom wall, said conduit having a second end attached to said sleeve adjacent to said lower edge, said conduit being angled downwardly from said pouch to said sleeve;

a collection bag being fluidly coupled to said lower edge of said sleeve to collect and retain urine;

a strap being attached to said sleeve adjacent to said upper edge, said strap being extendable around the penis and scrotum to retain said sleeve in place; and a resiliently stretchable band being attached to and extending along said top end of said pouch.

* * * * *